US008927475B2

(12) United States Patent
He et al.

(10) Patent No.: US 8,927,475 B2
(45) Date of Patent: Jan. 6, 2015

(54) CONSUMER PRODUCTS COMPRISING ALGAE DERIVED INGREDIENTS

(75) Inventors: Mengtao Pete He, Scottsdale, AZ (US); Paul A. Pappalardo, Scottsdale, AZ (US); Richard F. Theiler, Scottsdale, AZ (US)

(73) Assignee: The Dial Corporation, Scottsdale, AZ (US)

( * ) Notice: Subject to any disclaimer, the term of this patent is extended or adjusted under 35 U.S.C. 154(b) by 269 days.

(21) Appl. No.: 13/055,060

(22) PCT Filed: Aug. 6, 2009

(86) PCT No.: PCT/US2009/052929
§ 371 (c)(1), (2), (4) Date: Jan. 20, 2011

(87) PCT Pub. No.: WO2010/017346
PCT Pub. Date: Feb. 11, 2010

(65) Prior Publication Data
US 2011/0124544 A1    May 26, 2011

Related U.S. Application Data

(60) Provisional application No. 61/188,326, filed on Aug. 8, 2008.

(51) Int. Cl.
*A61Q 19/10* (2006.01)
*A61K 8/97* (2006.01)
*A61Q 5/02* (2006.01)
*C11D 3/382* (2006.01)

(52) U.S. Cl.
CPC ............... *A61Q 19/10* (2013.01); *A61K 8/975* (2013.01); *A61Q 5/02* (2013.01); *C11D 3/382* (2013.01)
USPC .......................... 510/130; 510/463; 510/506

(58) Field of Classification Search
None
See application file for complete search history.

(56) References Cited

U.S. PATENT DOCUMENTS

2004/0131580 A1 * 7/2004 Hagino et al. .................. 424/74
2007/0202126 A1   8/2007 Joerger et al.

FOREIGN PATENT DOCUMENTS

JP            62003791          *   1/1987

* cited by examiner

*Primary Examiner* — Necholus Ogden, Jr.
(74) *Attorney, Agent, or Firm* — David K. Benson (57) ABSTRACT

The present invention discloses bio-based consumer products formulated with at least one algae-derived ingredient that is either directly obtained from algae colonies or derived through standard synthetic organic transformations starting from bioorganic substances of algae origin.

14 Claims, 2 Drawing Sheets

CONSUMER PRODUCTS COMPRISING ALGAE DERIVED INGREDIENTS

CROSS REFERENCE TO RELATED APPLICATION

This is the U.S. national phase application of International Application No. PCT/US2009/052929, filed Aug. 6, 2009, which claims the benefit of U.S. Provisional Application No. 61/188,326, filed Aug. 8, 2008.

PRIORITY APPLICATION

The present application claims priority to U.S. Provisional Application 61/188,326 filed Aug. 8, 2008 and entitled "CONSUMER PRODUCTS COMPRISING ALGAE DERIVED INGREDIENTS", which is incorporated herein.

FIELD OF INVENTION

The present invention relates to consumer products formulated from bio-derived ingredients and more particularly to personal care, fabric care and hard surface cleaning compositions formulated with ingredients traceable to algae origin.

BACKGROUND

Algae have recently been in the news as a possible source of bio-fuels that may offer a replacement for fossil fuel. Indeed, with the recent soaring oil prices seen in 2008 and the grim numbers for proven oil reserves and projected oil reserves, bio-fuels are ever more frequently looked at as a necessary replacement for fossil fuels. However, most bio-fuel production competes with world food production, for example when bio-diesel is derived from crops such as rapeseed, corn, soybeans and the like. Thus, the most recent search for bio-fuel replacement of fossil fuel has turned to algae sources rather than food crops. Algae are well known for their fast growth rates, reaching 200 tons of algae mass per acre, which are at least one to two magnitudes higher than typical food-source plants. Most exciting is that growing algae in "bio-reactors" offers a method for scrubbing $CO_2$ from manufacturing plant effluent gas, and in this way the $CO_2$ that would ordinarily have gone straight into the atmosphere is re-routed to algae photosynthesis and reproduction. For example, U.S. Patent Application Publication 2007/0289206 (Kertz) presents a process and device for sequestering $CO_2$ using algae. The process utilizes a plurality of vertically suspended bioreactors to maximize efficiency of the photosynthesis reaction.

Through photosynthesis with $CO_2$ consumption, many species of algae produce and/or store a rich selection of bioorganic molecules including triglycerides, cellulose, alginates, agar carrageenan, sugars, glycoproteins, chlorophyll, astaxanthin, and a host of others. Many of these materials are used in industry directly (industrial gums such as agar, alginates and carrageenan) whereas others are in the spotlight as precursors to bio-fuel (particularly the lipids for algae-oil, and cellulose for subsequent hydrolysis and fermentation to ethanol).

Selection of algae species (natural and/or bioengineered, autotrophic or heterotrophic), and their growth conditions, together provide control in the variety of bioorganic materials available from the algae. These bioorganic materials may be extracted from the dried "algae mass", or may be found intracellularly or extracellularly stored, or even excreted as metabolites. For example, many companies continue to explore the dependence of both algae species and growth conditions on lipid yield. Generally speaking, algae appear to produce more highly unsaturated fiats than, animal or vegetable sources, similar to what is seen with other marine sources such as fish oil, and green algae appear best for shorter carbon chain lipid production. Additionally, some diatoms (*kontophyta*) are known to produce intracellular lipids. It appears that when some diatom species are raised in conditions of silica deprivation, sinking rates increase, and that in turn appears to trigger increased lipid production as a way to restore buoyancy.

Some algae and diatom species are known to produce more protein, carbohydrate and even hydrocarbon than lipids. For example, *Botryococcus* is a well known hydrocarbon producer where the bulk of its hydrocarbon is extracellularly located in the colony's matrix and in occluded globules. Some unique species of cyanobacteria (blue-green algae) have now been discovered by University of Texas-Austin researchers to continuously produce glucose, cellulose and sucrose as metabolites, thus obviating the need to destroy the organisms to harvest the useful bioorganic substances.

"Algae Extracts", which are often referred to as "Algae Colloid", are the chemicals directly extracted from blue, green and red algae through chemical or physical approaches. They are widely applied as food ingredients for human health and medical benefits, in cosmetic, household and personal care industry, some of those "Algae Extracts" such as carrageenan, a gelatinous material derived from *Chondrus crispus* and other species of red algae, is widely used as a thickening, stabilizing, emulsifying or suspending agent. Additionally, some species of dried marine micro-algae (e.g., *Schizochytrium* sp.) which is rich in the omega-3 long chain polyunsaturated fatty acid DHA (docosahexaenoic acid) is used as a food ingredient and supplement.

The prior art literature teaches methods of obtaining bioorganic substances from algae feedstock, with the end purpose of producing bio-fuels from the triglycerides or the saccharidic materials. In general, lipids may be extracted from algae and diatoms much in the same way oils are extracted from vegetative sources. That is, algae may be simply pressed, expeller pressed, solvent extracted (e.g., hexane), pressed then solvent extracted, critical fluid extracted, or in processes unique for algae, subjected to osmotic, sonicative or even enzymatic rupture of their cell walls in order to collect the lipids produced. Enzymatic processes may also be used on wet algae or dried algal mass to liberate cellulose, sugars and other bioorganic substances.

For example, U.S. Pat. No. 7,351,558 (Ruecker, et al.) claims a method for extracting lipids from algae species such as *Thraustochytrium* and *Schizochytrium* without the use of organic solvents. The patented method involves lysing the cells and a simple separation process.

Additionally, U.S. Patent Application Publication 2008/0160593 (Oyler) teaches a process for high-yielding micro-algae oil production comprising sequential photoautotrophic and heterotrophic reactions, followed by extraction of algae oil from the algae via a biological process. The Oyler application also teaches different routes of converting algae to algae lipid, and subsequently the algae lipid to bio-diesel, along with routes to convert algae to starch and cellulose and then ultimately to sugar.

U.S. Patent Application Publication 2008/0155888 (Vick, et al.) teaches the use of a mano-material to enhance the lipid oil extraction and purification from the crude biomass extract.

Finally, U.S. Pat. No. 7,135,308 and Application Publication 2007/0202582 (Bush, et al.) teach a process for the production of ethanol through fermentation of algae biomass in the presence of yeast.

Interestingly enough, the literature scantly mentions bio-derived chemicals, such as specialty chemicals, for non-food uses, where the organisms of origin are algae and where the biochemicals are not precursors intended for bio-fuel. The most relevant examples include U.S. Patent Application Publication 2008/0103340 (Binder, et al.) that teaches a process for producing bio-derived propylene glycol and ethylene glycol via hydrogenolysis along with an analytical test based on $C^{12}/C^{13}$ isotope ratio that may be used to substantiate that these materials are bio-derived.

Even more scant are references that teach non-food/non-fuel uses of bio-derived specialty chemicals. Of these few references, the most relevant is U.S. Patent Application Publication 2007/0202126 (Joerger et al.) that teaches botanical extracts, vegetal extracts, protein extracts, lipid extracts, marine extracts, algae extracts and milk extracts that are each combined with bio-derived 1,3-propane diol ("Bio-PDO") and/or an ester of Bio-PDO.

The references above and public knowledge in the field of algae research do not teach non-food, non-fuel consumer product formulations incorporating algae-derived functional ingredients and precursors obtained through autotrophic and/or heterotrophic processes. The published references do not teach the art of synergistically incorporating specific algae derived ingredients and specialty chemicals synthesized from algae precursors to create consumer products with superior properties in the areas of personal care (skin care and hair care), household care (hard surface cleaning, etc.), and fabric care.

SUMMARY OF THE INVENTION

The present invention comprises consumer product compositions that rely upon bioorganic materials extracted directly from algae and/or specialty chemicals synthetically derived from algal bioorganic substances, along with methods to produce these compositions Minimally the present invention is a portfolio of personal care products, fabric care products and hard surface cleaners that may comprise any one of surfactants, emollients, solvents, hydrocarbons, sugars and/or polysaccharides having carbon content substantially of algae origin.

DETAILED DESCRIPTION OF THE INVENTION

The following description is of exemplary embodiments only and is not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims. Additionally, though described herein in general terms of personal care, fabric care and hard surface cleaning compositions comprising bioorganic substances and specialty chemicals synthesized from algae-derived bioorganic substances, other consumer and institutional products relating to health and personal care, and home care, such as astringents, personal deodorants and antiperspirants, antibacterial agents, hard surface disinfectants and deodorizers, metal polishes, air treatment products, fabric and carpet stain removers, carpet cleaners, mechanical dishwashing detergents, rust removers, laundry starches, laundry sours, water-conditioners, and the like, fall within the ambit of the present invention provided that one or more components include an algae-derived ingredient.

The present invention may be more easily understood by reference to the following definitions:

As used herein, the term "bio-derived" means organic molecules derived from or synthesized from a renewable microbiological feedstock such as algae. The term "bio-derived" is meant to not only include bioorganic substances directly obtainable from an organism (from direct extraction for example), but also to include specialty chemicals that are indirectly obtained through standard synthetic organic transformations starting from bioorganic molecules obtainable from microbial sources. Thus, "bio-derived" molecules may include for example not only the naturally occurring lipids, cellulose, glycoproteins, sugars, and the like directly found in algal colonies, algal cells and dried algal mass, but also the fatty alcohols, fatty acid esters, sugars, ethanol, glycerol, and the like that may be obtained synthetically from the lipids, polysaccharides, etc., of algae.

As used herein, the term "petroleum-derived" means derived from or synthesized from petroleum or petroleum feedstock. For example, petroleum-derived specialty chemicals may be obtained through cracking of fossil hydrocarbons and oxidation or sulfonation of the resulting alkenes.

As used herein, the term "bio-based" means a product that is composed, in whole or in significant part, of bio-derived ingredients. Thus, bio-based consumer products may include a personal body wash comprised in significant part of surfactants, emollients and polymers that are bio-derived.

As used herein, in an "autotrophic process", algae produce complex organic compounds from $CO_2$ as the source of carbon, photo-synthetically.

As used herein, in a "heterotrophic process", algae produce complex organic compounds from non-photosynthetic sources of energy.

"Bio-Based Balance" (or BBB used herein) is stated as a weight percentage (%) of bio-derived carbon content of the finished bio-based consumer product. Thus for example, a hypothetical soap bar formulated entirely of 100% algae-derived fatty acid soap and glycerin (directly from algae lipid hydrolysis), the soap bar would have a "Bio Based Balance" of 100%. Note we have elected to eliminate the counter-ion from this calculation, seeing that it only takes into consideration the carbon. Addition of adjuvant such as fragrance, dyes, pigments, preservatives and the like will reduce the Bio-Based Balance down a small percentage from 100% since some of these functional materials are carbon containing and are obtained from petroleum sources. Additionally, a synthetic surfactant may have only the long carbon chain algae-derived and the remaining functionality petro-derived, which, will reduce the Bio-Based Balance of the consumer product from 100% total possible. For example, a $C_{18}$ fatty alkyl amidopropyl betaine with empirical formula $C_{25}H_{50}O_3N_2$ may have only its $[C_{18}H_{35}O]$ fragment algae-derived (from the algal triglyceride), in which case the molecule would have a 72 wt % Bio-Based Balance ($C_{18}/C_{25}$, or 216/300×100%=72%). Consequently this percentage would be factored into the total Bio-Based Balance for any composition utilizing this algae-derived betaine surfactant wherein only 18 of the total 25 carbons are algae-derived.

That said, the present invention is a portfolio of bio-based consumer products that comprise, in whole or in significant part, bioorganic substances directly obtainable from algae (from direct extraction for example), and/or specialty chemicals that are indirectly obtainable through standard synthetic organic transformations starting from bioorganic molecules that are in turn obtainable from algae. As mentioned above, some of the more practical starting materials directly obtainable from algae include lipids and polysaccharides, and these will be shown to be useful bio-derived feedstock for bio-derived specialty chemicals that may be used in consumer products. High yield, lipid-rich algae can be grown in water-ponds in temperature and environmentally controlled greenhouses and bioreactors. Through autotrophic and/or heterotrophic processes, the lipid oil can be extracted through the mechanical, chemical and biological techniques taught in the prior art and described above. Through algae strain selection, and technologies to influence the algae metabolic pathways, algae is also capable of producing high percentages of starch and cellulose via autotrophic and heterotrophic routes, giving additional feedstock for specialty chemicals used in consumer products.

In particular, hydrogenolysis, hydrolysis, amidation, esterification, ethoxylation and transesterification processes from algal lipid starting materials, along with the hydrolysis, enzymolysis, and/or fermentation of algal polysaccharides will be paramount routes to the production of an arsenal of specialty chemical and functional ingredients for consumer product formulation. Also the direct production of glucose, cellulose and sucrose as metabolites from living cyanobacteria give useful bioorganic ingredients and bio-feedstock for bio-derived specialty chemicals.

Algae that may be used to produce bioorganic substances that are directly incorporable into consumer products, or which are useful as precursors to bio-derived specialty chemicals include, but are not limited to, *Chlorophyta* (green algae), *Charophyta* (Stoneworts and Brittleworts), *Euglenophyta* (Euglenoids), *Chrysophyta* (golden-brown and yellow-green algae and diatoms), *Phacophyta* (brown algae), *Rhodophyta* (red algae), *Cyanophyta* (blue-green algae, same as blue-green bacteria or cyanobacteria), and the *Pyrrhophyta* (dinoflagellates). Most algae are photoautotrophs, and as mentioned, most dried algae mass, wet algae colonies, or algae metabolites will provide some levels of lipid, saccharidic substances including polysaccharides and sulfated materials (cellulose, hemicellulose, pectin, alginic acid, carrageenan, agarose, porphyran, fucelleran, funoran, starch, simple sugars, and the like), glycoproteins, and a variety of photosynthetic pigments (chlorophyll, astaxanthin, etc).

For algal lipid feedstock, some species of algae and diatom algae that may produce commercially significant levels of lipids include, but are not limited to; *Actinastrum; Actinochloris; Anbaena; Ankistrodesmus; Apatococcus; Asterarcys; Auzenochlorella; Bacilliarophy; Botrydiopsis; Botryococcus; Bractecoccus; Bumilleriopsis; Chaetophora; Chantransia; Characium; Chlamydomonas; Chlorella; Choridella; Chlorobotrys; Chlorococcum; Chorokybus; Chlorolumula; Chlormonas; Chlorophyceae; Chlorosarcinopsis; Chlorotatraedron; Chloricystis; Coccomyxa; Coelasrella; Coelastropsis; Coelastrum; Coenochloris; Coleochlamys; Cosmarium; Crucigenia; Crucigeniella; Desmodesmus; Diadesmis; Dictyococcus; Dictyosphaerium; Diplosphaera; Dunaliella; Ellipsoidion; Enallas; Eulia; Euglena; Fortiea; Genminella; Gonium; Grassiella; Haematococcus; Heterococcus; Interfilum; Isochrysis; Kentraspharera; Keratococcus; Klebsormidium; Koliella; Lagerheimia; Lobosphaera; Macrochloris; Microthamnion; Monodus; Monoraphidium; Mougeotia; Muriella; Mychonastes; Myrmecia; Nannochlolis; Nonnochlorpsis; Nautococcus; Navicula; Navioua; Neochloris; Neodesmus; Phaeodactylum; Pithophora; Pleurastrum; Pleurochrysis; Porphyridium; Possonia; Prasiolopsis; Protosiphon; Prymnesium; Pseudellipsoidion; Pseudendoclonium; Pseudocharaciopsis; Pseudococcomyxa; Pseudoendoclonium; Raphidocelis; Raphidonema; Rhexinema; Rhopalocystis; Scenedesmus; Schroederiella; Scotiella; Scotiellopsis; Selenastrum; Sphaerocystis; Spirogyra; Spirulina; Spongiochloris; Stichoccous; Stigeeoclonium; Synechoccus; Tetradesmus; Tetrahesron; Tertaselmis; Tertastrum; Tribonema; Vischeria; Willea; Xanthonema*; and *Zygnema*.

From these and other algae and diatom algae may be obtained lipid (or "algal fat") high in $C_{14}$ through $C_{22}$ triglycerides including saturated and unsaturated fatty acid chains. Other lipid and oil producing algae include blue algae, green algae, blue-green algae, and golden brown algae, often collectively referred to as micro-algae. This lipid constitution is similar to fresh water fish oils. Brown algae and red algae produce longer chain triglycerides, for example with carbon chains greater than 24-carbons.

Examples of Algae-Derived Surfactants

The algae-derived lipid oils (triglycerides), starch, and cellulose may be converted to algae-derived surfactants through established chemical synthetic routes, such as:

(1) Algae→Lipid Triglycerides→Surfactants;
(2) Algae→Starch or Cellulose→Sugar→Surfactants;
(3) Algae→Starch or Cellulose→Surfactants; and, combinations of the intermediates and end molecules obtainable from these basic routes, (e.g., a sugar from route 2 combined with a fatty acid from route 1 to produce an alkylpolyglycoside surfactant).

Figure 1:
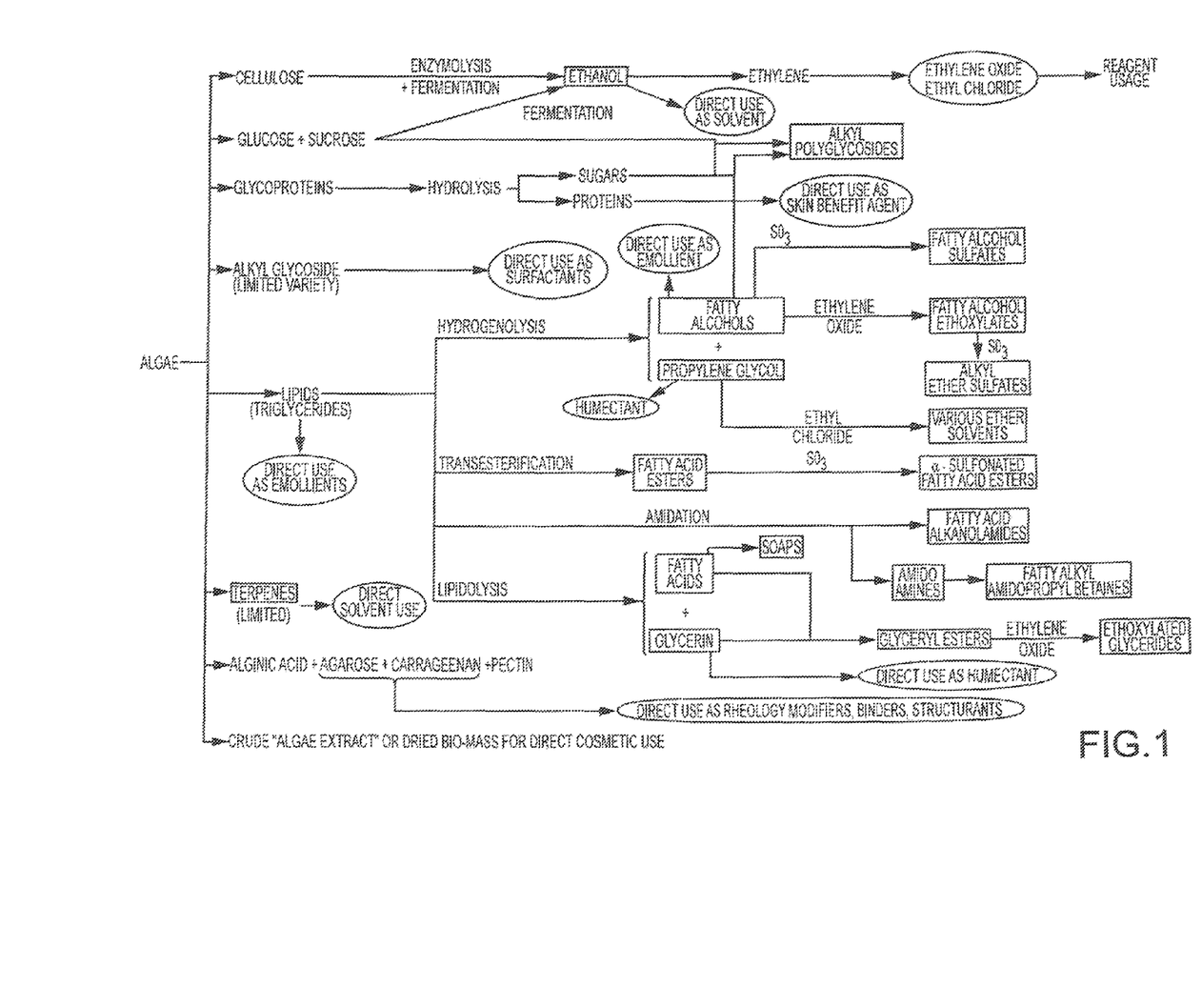
FIG. 1 depicts a flowchart of bioorganic substances directly obtainable from algae and specialty chemicals that may be synthesized from algae bioorganic substances.
Figure 2:
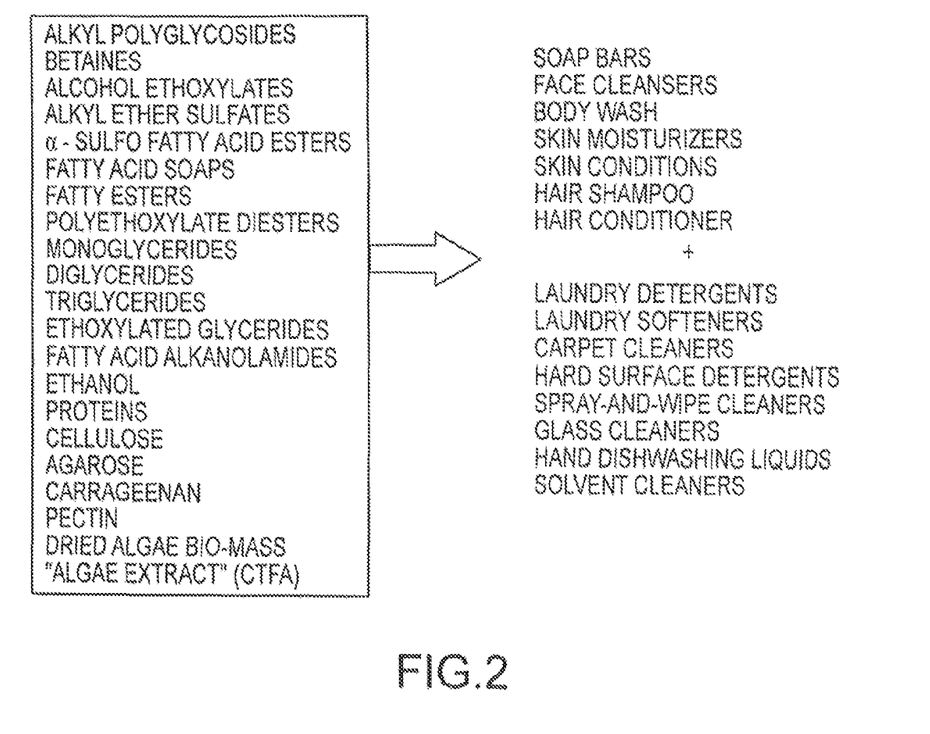
FIG. 2 depicts various consumer products available from algae bioorganic substances and bio-sourced specialty chemicals described in FIG. 1.

FIG. 1 shows in more detail the bioorganic materials available from algae and the synthetic organic transformations that may be used to produce specialty chemicals from the algal biochemicals. Examples of bio-derived surfactants, bio-derived emollients and other bio-derived functional materials having carbon chains traceable back to algae may include, but are not limited to, alkyl glycosides and alkyl polyglycosides, fatty alcohol ethoxylates, fatty acid soaps, fatty acid amides and alkanolamides, fatty amines and ethoxylated amines, quaternary ammonium compounds (cationic surfactants), fatty acid esters and ethoxylated esters, alpha-sulfonated fatty acid esters, fatty acid phosphates, glyceryl esters, glucamides, polyglycerol esters, lecithins, lignin sulfonates, proteins and protein derivatives, saponins, sorbitol and sorbitan esters, sucroglycerides, sucrose esters, alkyl sulfates and alcohol ether sulfates.

As will be described in more detail, TABLE 1 delineates some of the more important specialty chemicals that may be used in bio-based consumer product formulations, along with their accessibility from bio-derived intermediates. Some bioorganic materials, such as alkylglycosides, lignin, saponins, glycolipids (such as ascarosides, simplexides, plakopolyprenosides, and the like), etc. may or may not be found in algae species currently known to date, however some of these materials are known to be plant derived and may eventually be sourced from alga species that are currently undiscovered or not yet bio-engineered. For example, certain alkylglycosides are found naturally in cyanobacteria, but lignin is primarily found in wood. Of course, it is important to realize that dried algae mass itself may form a skin nutrient/supplement that may be incorporated directly into bio-based personal care products "as is", (e.g., added directly into leave-on or rinse-off personal cleansing, hair shampoos, skin or hair conditioning products). In this way, a personal care consumer product may be formulated using bio-derived specialty chemicals plus actual dried algae.

TABLE 1

Routes to Bio-Derived Specialty Chemicals

| Bio-derived Specialty Chemical | Route to the primary C-chain | Further reactions to final chemical |
|---|---|---|
| Fatty Acid Soaps<br>$R-CO_2M$ | Saporification of algae lipid and separation of the fatty acids from the glycerol. | Neutralization of fatty acids with various alkaline materials to produce desired counter-ion "M". |
| Alpha-Sulfonated Fatty Acid Esters<br>$R^1-CH(SO_3Na)-CO_2-R^2$ | Transesterification of algae lipid with alcohol and sulfonation with $SO_3$. The ethyl ester ($R^2$ = ethyl) is preferred, with transesterification using ethanol from algal saccharide fermentation. | n/a |
| Fatty Alcohol Ethoxylates<br>$R-O-(CH_2CH_2O)_3-H$ | a. Saponification of algae lipid and catalytic hydrogenation of the free fatty acids; or<br>b. Transesterification of algae lipid with alcohol and catalytic hydrogenation of the resulting fatty acid esters; or<br>c. Direct hydrogenation of algae lipids and separation of fatty alcohols from propane diol. | Ethoxylation with either petro-derived or bio-derived ethylene oxide.<br>Preferred ethylene oxide is prepared from ethanol, which is a product of algal polysaccharide fermentation. |
| Alkyl Sulfate<br>$R-O-SO_3-M$ | Fatty alcohol chain (R—OH) is algae-derived as described above. | Sulfonation of the algae-derived fatty alcohol. |
| Alkyl Ether Sulfate<br>$R-O-(CH_2CH_2O)_x-SO_3M$ | Fatty alcohol chain (R—OH) is algae-derived as described above. | Ethoxylation with either petro-derived or bio-derived ethylene oxide followed by sulfonation.<br>Preferred ethylene oxide is prepared from ethanol, which is a product of algal polysaccharide fermentation. |
| Fatty Acid Amides and Alkanolamides<br>$R-CO-NR^1R^2R^3$ | Direct amidation of algae lipids with ammonia, amines or alkanolamines. | n/a |
| Fatty Acid Amines<br>$R-CH_2-NR^1R^2$ | Saponification of algae lipid to free fatty acids followed by reaction with ammonia and hydrogen, (to the primary fatty amine, $R^1$ and $R^2$ = H). | Alkylation of the primary fatty amine to secondary or tertiary fatty amines.<br>Reaction of tertiary amine with methyl sulfate or methyl chloride produces quaternary ammonium compounds. |
| Alkylglycosides and alkyl polyglycosides<br>$R-O-(C_6H_{10}O_5)_x-H$ | a. Extracted directly from several species of cyanobacteria e.g. *Anabaena cylindrica*; or<br>b. Fatty alcohol chain (R—OH) is algae-derived as described above. | Reaction of algae-derived glucose (cellulolysis of algal cellulose) with the above described algae-derived fatty alcohol under acid catalysis. |
| Ethoxylated Fatty Amines<br>$R-NH-(CH_2CH_2O)_x-H$, and<br>$R-N-[(CH_2CH_2O)_x-H]_2$ | Fatty amine ($R-NH_2$) is obtained from algal fats, ammonia and hydrogen as described above. | Ethoxylation with either petro-derived or bio-derived ethylene oxide followed by sulfonation.<br>Preferred ethylene oxide is prepared from ethanol, which is a product of algal polysaccharide fermentation. |
| Fatty alkyl amidopropyl betaine<br>$R-C(=O)-NH-(CH_2)_3-N^+(CH_3)(CH_2)-CH_2-COO^-$ | Direct amidation of algae lipids with 1,3-propanediamine to produce the amidoamine:<br>$R-CO-NH-[CH_2]_3-NH_2$ | Reaction of the amidoamine with methylchloride and chloroacetic acid. |

For example, a surfactant well known and used in a host of consumer products includes the alkylpolyglycoside nonionic surfactants. The alkyl polyglycosides (commonly referred to as, APG's), also called alkyl polyglucosides if the saccharide moiety is glucose, are naturally derived, nonionic surfactants. Interestingly enough, some alkyl glycosides and polyglycosides occur in nature, e.g., in cyanobacteria such as *Anabaena cylindrica*, *Anamaeba torulosa*, and *Cyanospira rippkae* where they may take part in cell protection However, synthetic alkyl polyglycosides that may be used in the bio-based consumer products of the present invention may be more practically conceived as fatty ester derivatives of saccharides or polyglycosides that are formed when a carbohydrate is reacted under acidic conditions with a fatty alcohol through condensation polymerization. The APG's are typically derived from corn-based carbohydrates and fatty alcohols from natural oils found in animals, coconuts and palm kernels. However, these surfactants may be constructed with algae-derived bioorganics. As described above, glucose may be directly obtained from algae, or alternately the sugars used to synthesize APG surfactants may be derived from cellulose or other algal polysaccharides. The fatty alcohols may be obtained by hydrolysis or transesterification of algae lipids followed by hydrogenation of the intermediate fatty acids or fatty acid esters. Such methods for deriving APG's from vegetative sources are well known in the art and may be extrapolated to algae-sourced, rather than crop-sourced, bioorganic substances. The alkyl polyglycosides that are preferred for use in the present invention contain a hydrophilic group derived from carbohydrates and is composed of one or more anhydroglucose units. Each of the glucose units may have two ether oxygen atoms and three hydroxyl groups, along with a terminal hydroxyl group, which together impart water solubility to the glycoside. The presence of the alkyl carbon chain leads to the hydrophobic tail of the molecule.

When carbohydrate molecules react with fatty alcohol compounds, alkyl polyglucoside molecules are formed having single or multiple anhydroglucose units, which are termed monoglycosides and polyglycosides, respectively. The final alkyl polyglucoside product typically has a distribution of glucose units (i.e. degree of polymerization).

The APG's that may be used in the consumer products of the present invention preferably comprise saccharide or polysaccharide groups (i.e., mono-, di-, tri-, etc. saccharides) of hexose or pentose, and a fatty aliphatic group having 6 to 20 carbon atoms. Preferred allyl polyglycosides that can be used according to the present invention are represented by the general formula, $G_x$-O—$R^1$, wherein G is a moiety derived from reducing saccharide containing 5 or 6 carbon atoms, e.g., pentose or hexose; $R^1$ is fatty alkyl group containing 6 to 20 carbon atoms; and x is the degree of polymerization of the polyglucoside, representing the number of monosaccharide repeating units in the polyglucoside. Generally, x is an integer on the basis of individual molecules, but because there are statistical variations in the manufacturing process for APG's, x may be a non-integer on an average basis when referred to particular APG's of use as an ingredient for the bio-based consumer product compositions of the present invention. For the APG's preferred for use herein, x preferably has a value of less than 2.5, and more preferably is between 1 and 2. Exemplary saccharides from which G can be derived are glucose, fructose, mannose, galactose, talose, gulose, allose, altrose, idose, arabinose, xylose, lyxose and ribose. Because of the ready availability of glucose from algae, glucose is preferred in polyglycosides. As mentioned, glucose may be obtained as a metabolite from certain cyanobacteria or may be obtained by cellulolysis (chemically or enzymatically) of algal cellulose. The fatty alkyl group is preferably saturated, although unsaturated fatty chains may be used. Generally, the commercially available polyglycosides have $C_8$ to $C_{16}$ alkyl chains and an average degree of polymerization of from 1.4 to 1.6, and these may be readily synthesized from algae-derived intermediates rather than crop-based substances.

As shown in FIG. 1, another example of a surfactant obtainable through synthetic organic transformations starting from algae bioorganic materials includes the fatty alcohol ethoxylates. These preferred nonionic surfactants include ethoxylated and/or propoxylated primary alcohols having 12 to 18 carbon atoms and on average from 4 to 12 moles of ethylene oxide (EO) and/or from 1 to 10 moles of propylene oxide (PO) per mole of alcohol. Algae-derived examples may include alcohol ethoxylates containing linear radicals from alcohols of bio-origin having 14 to 24 carbon atoms, e.g., from the hydrogenation of fatty acids and/or fatty acid esters that are in turn derived from algal lipids through hydrolysis or transesterification, respectively. Fatty alcohols may also be obtained by direct high-pressure hydrogenation of the algae lipid mass and separation of the fatty alcohols from the propane diol. Of course, the ethoxylation or the propoxylation (preferably on average from 4 to about 12 EO, PO, or EO/PO per mole of alcohol) doesn't necessarily have to come from bio-sources, although that would be preferred. So for example, a fatty alcohol with carbon chain directly from algae sources may be conventionally ethoxylated with ethylene oxide obtained from petroleum sources (cracked ethylene and oxygen). In this way, a preferred detergent surfactant such as $C_{14}$-$C_{16}$ alcohol ethoxylate-7EO would at least have about 50% of the carbon (the $C_{14}$-$C_{16}$ chain) obtained from algae, and about 50% of the carbon from petroleum sources (the 7EO, or 14-carbons from the n-moles of ethylene oxide). More preferred is to incorporate bio-derived ethylene oxide as the building blocks for the ethoxylate (EO) chains of these nonionic surfactants to create molecules having all of the carbon bio-derived. In known processes, bio-derived ethanol may be dehydrated to ethylene, which may in turn be oxidized to ethylene oxide with oxygen. Additionally, once fatty alcohols are obtained from algae lipids, the alcohols may be reacted in a Guerbet Reaction ("Guerbetization") to produce the branched "Guerbet Alcohols" which then may be ethoxylated to give bio-derived branched chain alcohol ethoxylate surfactants.

Also shown in FIG. 1, another surfactant derivable from algae sources include the fatty acid soaps, and these anionic surfactants are particularly important in the formulation of bio-based consumer products such as personal cleansing body wash and bar soap, laundry detergents and hard surface cleaners. As used herein, "fatty soap" means the salts of fatty acids. For example, the fatty soaps that may be used here have general formula R—$CO_2$ M, wherein R represents a algae-derived linear alkyl (saturated or unsaturated) group having between about 8 and 24 carbons and M represents an alkali metal such as sodium or potassium or ammonium or alkyl- or dialkyl- or trialkyl-ammonium or alkanolammonium cation. The fatty acids of particular use in the consumer products of the present invention include carbon chains of from about 8 to about 24 carbon atoms, preferably from about 10 to about 20 carbon atoms and most preferably from about 14 to about 18 carbon atoms. Preferred fatty acids for use in the present invention should have similar structure to the animal derived tallow or hydrogenated tallow fatty acids and their preferred salts (soaps) are alkali metal salts, such as sodium and potassium or mixtures thereof. That being said, hydrolysis of algae lipids will produce a mixture of unsaturated fatty acids and glycerol and the unsaturated fatty acids may in turn be hydrogenated as necessary to arrive at more saturated fats. Well known are purification processes such as distillation to arrive at particular tatty acid distribution. So for example, crude algae triglyceride may be transesterified with methanol and the resulting fatty acid methyl esters mixture may be fractionally distilled. The resulting methyl ester distillate "cuts" may then be hydrolyzed to yield fatty acids with narrower carbon chain distributions.

As discussed below, the glycerol may have separate uses, or as is well known in soap manufacturing, may be directly incorporated into personal cleansing body washes and bar soaps. Other useful soaps are ammonium and alkanol ammonium salts of fatty acids that may be obtained by neutralization of the algae-derived fatty acids with ammonia or a suitable alkanolamine.

Still referring to FIG. 1, another bio-derived anionic surfactant that may find use in the compositions of the present invention includes the alpha-sulfonated alkyl esters, which are the linear esters of $C_6$-$C_{22}$ carboxylic acids sulfonated with gaseous $SO_3$. Alpha, (or α-used interchangeably herein), pertains to the first position on the carbon chain adjacent to the carboxylate carbon, as per standard organic chemistry nomenclature. The alpha-sulfonated alkyl esters may be pure alkyl ester or a blend of (1) a mono-salt of an alpha-sulfonated alkyl ester of a fatty acid having from 8-20 carbon atoms where the alkyl portion forming the ester is straight alkyl chain of 1-6 carbon atoms and (2) a di-salt of an alpha-sulfonated fatty acid, the ratio of mono-salt to di-salt being at least about 2:1. The alpha-sulfonated alkyl esters useful herein are typically prepared by sulfonating an alkyl ester of a fatty acid with a sulfonating agent such as $SO_3$. As mentioned above, the fatty acid esters are most readily available by transesterification of algae lipids, or alternatively by esterification of the fatty acids obtained by hydrolysis of the algae lipids. When prepared by sulfonation of fatty acid esters, the alpha-sulfonated alkyl esters normally contain a minor amounts (typically less than 33% by weight), of the di-salt of the alpha-sulfonated fatty acid which results from saponification of the ester. Preferred alpha-sulfonated alkyl esters contain less than about 10% by weight of the di-salt of the corresponding alpha-sulfonated fatty acid.

The preferred alpha-sulfonated fatty acid ester surfactants that may be incorporated into the consumer product compositions of the present invention comprise alkyl ester sulfonate surfactants of the structural formula $R^3$—$CH(SO_3M)$-$CO_2R^4$, wherein $R^3$ is a $C_8$-$C_{20}$ algae-sourced carbon chain, $R^4$ is a straight or branched chain $C_1$-$C_6$ alkyl group and M is a cation which forms a water soluble salt with the alkyl ester sulfonate, including sodium, potassium, magnesium, and ammonium cations. Preferably, $R^3$ is $C_{10}$-$C_{16}$ fatty alkyl, and $R^4$ is ethyl, in turn indirectly derived from algal polysaccharides (transesterification of the algae-lipid with ethanol obtained through algae cellulose fermentation). Most preferred are alpha-sulfonated ethyl esters of a distribution of fatty acids having an average of from 12 to 16 carbon atoms.

Additional bio-derived anionic surfactants useful in the bio-based consumer product compositions herein, are the alkyl ether sulfates, also known as alcohol ether sulfates Alcohol ether sulfates are the sulfuric monoesters of the straight chain alcohol ethoxylates and have the general formula R—$(CH_2CH_2O)_x$—$SO_3M$, where R—$(CH_2CH_2O)_x$— preferably comprises $C_6$-$C_{21}$ alcohol ethoxylated with from about 0.5 to about 9 mol of ethylene oxide (x=0.5 to 9 EO), such as $C_{12}$-$C_{18}$ alcohols containing from 0.5 to 9 EO, and where M is alkali metal or ammonium, alkyl ammonium or alkanol ammonium counterion. Preferred alkyl ether sulfates include $C_8$-$C_{18}$ alcohol ether sulfates with a degree of ethoxylation of from about 0.5 to about 9 ethylene oxide moieties and most pre erred are the $C_{12}$-$C_{16}$ alcohol ether sulfates with ethoxylation from about 4 to about 9 ethylene oxide moieties, with 7 ethylene oxide moieties being most preferred. It is understood that when referring to alkyl ether sulfates, these substances are already salts (hence "sulfonate"), and most preferred and most readily available are the sodium alkyl ether sulfates (also referred to as NaAES). As shown in FIG. 1, the alkyl ether sulfates are readily obtainable by sulfonation of the bio-sourced alcohol ethoxylates described above.

Other anionic surfactants that may be included in the bio-based consumer product compositions herein include the alkyl sulfates, also known as alcohol sulfates. These surfactants have the general formula R—O—$SO_3Na$ where R is from about 10 to 18 carbon atoms, and these materials may also be denoted as sulfuric monoesters of $C_{10}$-$C_{18}$ alcohols, examples being sodium decyl sulfate, sodium palmityl alkyl sulfate, sodium myristyl alkyl sulfate, sodium dodecyl sulfate, sodium tallow alkyl sulfate, sodium coconut alkyl sulfate and mixtures of these surfactants, or of $C_{10}$-$C_{20}$ oxo alcohols, and those monoesters of secondary alcohols of this chain length. From a consumer detergents standpoint, $C_{12}$-$C_{16}$-alkyl sulfates are preferred. As shown in FIG. 1, the alkyl sulfates are readily obtainable by sulfonation of the bio-sourced fatty alcohols described above, which are most directly synthesized through hydrogenolysis of the algae lipids, or less directly through transesterification of the algae lipids and hydrogenation of the intermediate fatty acid esters.

The bio-based consumer product compositions of the present invention may also include bio-derived amide type nonionic surfactants, far example alkanolamides that are condensates of algae-derived fatty acids with alkanolamines such as monoethanolamine (MEA), diethanolamine (DEA) and monoisopropanolamine (MIPA), that have previously found widespread use in cosmetic, personal care, household and industrial formulations. Useful alkanolamides include ethanolamides and/or isopropanolamides such as monoethanolamides, diethanolamides and isopropanolamides in which the fatty acid acyl radical typically contains from 8 to 18 carbon atoms. Especially satisfactory alkanolamides have been mono- and diethanolamides such as those derived from mixed fatty acids or special fractions containing, for instance, predominately $C_{12}$ to $C_{14}$ fatty acids. For most consumer product detergent applications, alkanolamides ides prepared from algal trialkylglycerides may be of acceptable quality. For example, and as shown FIG. 1, bio-derived fatty acids may be obtained from algae lipids through a number of routes, and these may be amidated with the required alkanolamine. Alternatively, and more directly, the nonionic alkanolamides may be obtained by direct amidation of the algae lipid (e.g., the crude algae fat).

Additional classes of bio-derived nonionic surfactants that may be used in the bio-based consumer product detergent compositions herein include ethoxylated fatty acid alkyl esters, preferably having 1 to 4 carbon atoms in the alkyl chain, especially fatty acid ethyl esters. Most preferred is to ethoxylate an algae-sourced fatty acid ester with ethylene oxide that in turn was obtained from algae-sourced ethanol. Additionally, ethoxylated fatty amines are useful in consumer products and these may be obtained by ethoxylation of fatty amines, wherein these starting materials are obtained from ethanol and algae lipid, respectively.

Lastly, fatty alkylamidopropyl betaines represent an important class of mild detergents that find prominent use in personal bodywash and shampoo formulations. Indeed, cocamidopropyl betaine, with or without sodium laureth sulfate as co-surfactant, is the surfactant system of choice for most shampoo and bodywash compositions. The synthesis of betaines is well known and is described in U.S. Pat. No. 5,354,906 (Weitemeyer, et al.) incorporated herein in its entirety by reference. The amidoamine intermediates described by Weitemeyer as obtainable from coconut fatty acid are just as easily be obtainable from a tatty acid blend derived from hydrolysis or hydrogenolysis of algal lipids. Alternatively, algae lipids may be directly amidated using 1,3-propanediamine to give fatty amidoamines that then may be converted to alkylamidopropyl betaines using the methods described in the '906 patent.

Examples of Algae-Derived Solvents

As discussed above, bio-derived ethanol is readily obtainable through fermentation of algae-derived cellulose, with or without an enzymatic pre-digestion step to the monosaccharide mixture. Additionally as mentioned, 1,3-propane diol is readily obtained from hydrogenolysis of algae-lipid (separating off the fatty alcohols for surfactant use). What is important to note is that once ethanol and 1,3-propane diol are obtained from algae, a number of other solvents are available through synthetic organic transformations using these intermediates. For example, ethanol may be converted to ethyl chloride and that may be reacted with 1,3-propane diol to yield either propylene glycol monoethyl ether or propylene glycol diethyl ether. Of course, not being restricted to total reliance on algae-derived carbon, methyl ethers such as propylene glycol monomethyl ether and propylene glycol dimethyl ether are easily obtainable from algae-derived 1,3-propane diol and methyl chloride that is petro-derived. Many other solvents are envisioned as being algae-derived, such as the di- and tri-propylene glycol mono and di-ethers, amongst others.

Examples of Algae-Derived Emollients, Moisturizers and Other Skin Benefit Agents In addition to alga-derived surfactants as delineated above, which are useful in both detergents and personal skin/hair cleansing compositions, personal care consumer products such as liquid body wash, toilet soap and shampoo may also comprise emollients, moisturizers, humectants, and other skin benefit agents. Many of these functional materials that find use in personal care formulations may be obtained either directly or indirectly from algae. Indeed, algae biomass is currently used in dry form or as an extract in personal cat cosmetics as rheology modifiers, humectants, and antioxidants. For example, algae-derived lipids and cellulosic bioorganic ingredients are well known skin benefit agents, with advantages including but not limited to skin moisturizing, antioxidation, anti-aging, anti-drying, toning, and anti-wrinkle properties. Some algae species typically fund in cosmetics include, but are not limited to; *Ulva lactuca, Ascophyllum, Laminaria longicruris, Laminaria saccharine, Laminaria digitata, Alaria esculenta,* various *Porphyra* species, *Chondrus crispus,* and *Mastocarpus stellalus*. The CTFA (Cosmetics, Toiletries & Fragrance Association) currently Lists "algae extract" for cosmetic use, and now requires that personal care manufacturers list the specific strains of algae used in their products. Algae biomass for cosmetic use is available from a variety of suppliers, for example Fitoplancton Marino, Spain.

Emollients are substances that soften and soothe human skin, whereas moisturizers are substances that actually promote transfer of water into the skin. Related to moisturizers are humectants, which are hygroscopic materials capable of transferring bound water into skin layers. Personal care products often incorporate emollients, humectants and moisturizers together. As mentioned above, "algae extract", a crude extract of algae biomass without regard to the distribution of functional biomaterials, is used in personal care cosmetics and other skin care products.

As an alternative to incorporation of "algae extract" into personal care compositions, more refined materials may be isolated from algae biomass, and further functional materials may be obtained synthetically from these naturally occurring bioorganic substances. The following flowcharts show general routes to skin benefit agents from algae feedstock:

(1) Algae→Triglycerides→Other Skin Benefit Agents (2) Algae→Starch or Cellulose→Other Skin Benefit Agents As mentioned above for surfactants, selection of algae species along with adjustment of growth conditions can alter the amounts of lipid, polysaccharide, and other bioorganic substances. Some of these materials (for example, algae lipid, or purified glycerol from lipidolysis of algal lipid) may be incorporated directly into personal care products for various effects such as moisturization. Other materials may be obtained through standard organic reactions beginning with algae lipid or algae polysaccharides. Some of the more important materials are shown in TABLE 2.

Examples of algae-derived skin benefit agents include, but are not limited to, fatty acid, fatty acid esters, sorbitan fatty acid esters, glycerol, glyceryl esters (e.g., glyceryl triacetate), lecithin, fatty alcohol, propylene glycol, sorbitol, xylitol, manitol, and fatty acid mono-, di- and triglycerides. Additional nonionic polyether materials that may find use in bio-based consumer personal care products as emollients, moisturizers, humectants, and other substances to impart better "feel" to both skin/hair and the composition itself include polyethers such as polyoxyethylene cetyl ethers, polyoxyethylene oleyl ethers, polyoxyethylene stearyl ethers, polyoxyethylene lauryl ethers, polyoxyethylene isocetyl ethers, polyoxyethylene isostearyl ethers, polyoxyethylene octydodecyl ethers, polyoxyethylene behenyl ethers, polyoxyethylene decyltetradecyl ethers, polyoxyethylene cholesteryl ethers, polyoxyethylene-polyoxypropylene ethers. Also the ester type products such as propylene glycol fatty acid esters, ethylene glycol fatty acid esters, and the like. Also, the ether-ester type emulsifiers may find use here as well, including such nonionic materials as polyethyleneglycol monostearates, polyethyleneglycol monooleates, polyethyleneglycol monolaurate, polyoxyethylene hydrogenated fatty oils, polyoxyethyl ene glyceryl monostearates, polyethyleneglycol monoisostearates polyoxyethylene castor oils, polyoxyethylene cetyl ether stearates, polyoxyethylene stearyl ether stearates, polyoxyethylene lauryl et her stearates, polyoxyethylene lauryl ether isostearates, polyethyleneglycol dilaurates, polyethyleneglycol distearates, polyethyleneglycol diisostearates, polyethyleneglycol dioleates, polyethylene sorbitan fatty acid esters, and polyethylene sorbitan fatty acid esters, and the like. Many of these materials are obtainable from algae-sourced bioorganic substances through well known synthetic organic transformations.

TABLE 2

ROUTES TO ALGAE-DERIVED EMOLLIENTS, MOISTURIZERS, AND OTHER SKIN BENEFIT AGENTS.

| Bio-derived Functional Material | Route to the primary C-chain | Further reactions to final chemical |
|---|---|---|
| Fatty Acid Esters $R^1$—$CO_3R^2$ | Transesterification of algae lipid with corresponding alcohol | n/a |

TABLE 2-continued

ROUTES TO ALGAE-DERIVED EMOLLIENTS, MOISTURIZERS, AND OTHER SKIN BENEFIT AGENTS.

| Bio-derived Functional Material | Route to the primary C-chain | Further reactions to final chemical |
|---|---|---|
| | $R^2$—OH. If $R^2$—OH is ethanol, this may be derived from fermentation of algal polysaccharide. | |
| Fatty Acid Triglycerides ("Algae fat" or "algae lipid") | Direct extraction from algae biomass. | n/a |
| Fatty Acid Mono- and Di-Triglycerides | Extraction of algal fat followed by controlled lipolysis with select lipase enzymes; or Reaction of algae-derived glycerol with algae-derived fatty acids (Table 1). | n/a |
| Glycerin | Hydrolysis of algal lipid, or algal biomass followed by distillation. May also be obtained through enzymatic lipidolysis. | n/a |
| Polyoxyethylene fatty alkyl ethers (fatty alcohol ethoxylates-high EO) (e.g. $C_{12}$ alcohol-23 Mole EO) | As per TABLE 1, synthesis of fatty alcohols such as $C_{12}$-$C_{18}$ saturated and/or unsaturated alcohols. | As per TABLE 1, ethoxylation with petro- or algal derived ethylene oxide. High degree of ethoxylation is required for humectants, (e.g. 20-200 mole EO). |

Examples of Algae-Based Stucturants, Rheology Modifiers and Fillers

The algae-derived lipid starch, cellulose and sulfated polysaccharides can be directly added to bio-based personal care compositions or converted into suitable thickeners, structurants, rheology modifiers and fillers for non-food consumer products having any physical form (solid, powder, gel and liquid).

(1) Algae→Triglycerides→Other Formulation Structurants and Fillers (2) Algae→Starch or Cellulose→Other Formulation Structurants and Fillers Examples of those algae-derived formulation structurants, rheology modifiers and fillers include but not limited to agarose, carrageenan, cellulose, starch, carboxymethyl cellulose, fatty acids, glycerol, fatty alcohols, triglycerides, and triglyceride esters.

Bio-Based Consumer Product Formulations Based on Algae-Derived Ingredients

In the present invention, the bio-based consumer product formulations are comprised, in whole, or in significant part, of said algae-derived surfactants, emollients and other skin benefit agents, and structurants, rheology modifiers and fillers as described above. Preferably the algae-derived materials are combined in specifically optimized weight ratios, or used as mixtures found directly from algae in various combinations and weight rations, via said autotrophic or heterotrophic processes. Such mixtures of algae-derived functional ingredients at targeted weight ratios provide for consumer product formulations used in personal care household care and laundry care.

It must be stressed that the actual chemical structures of the above mentioned specialty chemicals and the structures of the bioorganic molecules from algae may be variable, based on the alga species and the growth conditions. For example, the fatty alcohol building blocks (R—OH) mentioned above, preferably prepared by hydrolysis and catalytic hydrogenation of algae lipid feedstock, may comprise considerably variable fatty "R-groups" based on the alga species/strain and growth conditions (light, temperature, nutrients, etc.) chosen, and where these species and growth conditions may heretofore be unknown and as yet unexplored. Thus, now and particularly in the future it may be possible to select new alga species and their growth conditions to generate sources of very specific fatty alkyl carbon-chain feedstock from algal lipid. Of course, as with vegetable and animal derived fatty alkyl chains today (coconut, palm, tallow, and the like), carbon chain length distributions are expected and entirely acceptable. Thus, when hydrolysis of algae triglyceride feedstock generates primarily $C_{16}$/$C_{18}$ unsaturated fatty acids, this distribution may be used directly into soap formulations or channeled as is into synthetic surfactant syntheses.

Additionally it must be stressed that some combinations of bioorganic materials directly obtainable from said autotrophic or heterotrophic processes may be ready or almost ready for consumer applications. This approach provides cost savings and low environmental impact to the manufacturing processes when compared to conventional methods. As mentioned above one of the simplest examples is to directly use the hydrolysis mixture of algal triglyceride into soap, (i.e., using the glycerin and fatty acid mixture without separation). The ultimate goal of formulating bio-based consumer non-food/non-fuel products with high Bio-Based Balance is to reduce the reliance on synthetic organic chemistry and to rely more and more on bioorganic substances and mixtures directly found in the algae. However, with existing alga strains and common organic reactions as shown in TABLE 1, all of the critical consumer product ingredients are achievable, albeit with varying degrees of reliance on petroderived carbon. Any of the bio-based consumer product compositions of the present invention may of course be supplemented with conventional surfactants and/or functional ingredients obtained from petroleum sources as needed so long as the final composition is substantially comprised of bio-derived ingredients. It is anticipated that pigments, optical brighteners, preservatives and the like may still need to be added to certain consumer products, and these materials may need to be synthetically derived from petroleum.

Utilizing algae-derived ingredients far consumer product formulation may reduce the overall energy requirements in the consumer products industry. For example, to supply consumer packaged goods conventionally the approach today is normally:

Petroleum Refining and Cracking→Transportation→Specialty Chemicals Manufacturing→Transportation→End Formulator→Packaging→Shipping→Distribution. Whereas an algae-based consumer products formulation may eliminate some of the energy-demanding steps as follows:

Algae→autotrophic or heterotrophic growth→Bioorganic Chemicals Mixture→End Formulator (with minimal synthetic materials)→Packaging→Shipping→Distribution. The emphasis being that bio-engineered mixtures of biochemicals can reduce the reliance on synthetic specialty chemicals, consequently not only reducing or eliminating the reliance on petroleum feedstock, but also reducing the intermediate transportation burden. Obviously the greater the reliance on algae-derived bioorganic mixtures that can be directly used in a consumer product composition without further synthetic modification, the greater the reduction in both energy usage and environmental impact.

Examples of Bio-Based Consumer Products

TABLE 3 shows non-limiting examples of preferred embodiments of the present invention wherein algae-derived ingredients are used to create a variety of consumer products. It is understood that the wide ranges shown for the fatty alkyl chains in the algae-derived surfactants, ($C_{14}$-$C_{24}$, for example), are not to be taken as what the surfactant distribution is precisely when incorporated into the composition. Rather, the preferred surfactant distributions lay within this wide range of carbon chain distribution. As explained above, the fatty carbon chain distributions may be narrowed by prior distillation of the fatty acid methyl esters (obtainable by transesterification of algae-lipid with methanol), followed by hydrolysis (to the fatty acids) or hydrogenation (to the fatty alcohols). Additionally, the unsaturation in the fatty chains may be control led by hydrogenation.

Each of the example composition in TABLE 3 has Bio-based Balances that may be supported by the established experimental approaches testing the $C^{12}/C^{13}$ isotope ratio. The BBB's are estimated at best, since the example formulations, are shown with ranges of ingredients, plus the surfactants may have combinations of petro- and algae-derived carbon as discussed thoroughly above. That is, much higher BBB percentages are possible if the ethoxylation in some of these surfactants is through reaction with ethylene oxide that is algae-derived rather than petro-derived. Additionally, the betaines and the fatty acid diethanolamides have carbon extraneous to the fatty alkyl chains that may or may not be algae-derived. Thus, any of these surfactant molecules can be between about 60% and 100% Bio-Based Balance wt, percent depending on the need for derivatization with petro-derived reactants.

The actual formulation of the bio-based consumer products is through standard methods of manufacturing. For example, soap bars or "toilet soap", is made by plodding soap mixtures, extruding the soap, cutting it and die-stamping it into bars. Alternatively some soap bars are poured into molds rather than extruded and stamped. All the liquid formulations disclosed herein are easily made in batch mixtures, with addition of water usually first such that the liquid is above the mixing impeller within the tank. Then the specialty chemicals such as the surfactants are added, followed by the dyes and preservative. These methods of manufacture have been around for more than a century and are well known.

We have herein disclosed new bio-based consumer products comprising algae-derived ingredients. The most preferred bio-based consumer products incorporate bioorganic materials directly obtainable from algae. Also preferred are bio-based consumer products that incorporate at least one specialty chemical ingredient such as a surfactant obtainable

TABLE 3

BIO-BASED CONSUMER PRODUCT EXAMPLES

| Consumer Product | Suggested Bio-Based Formulation (wt % actives) (* indicates algae-derived carbon chains) | | Bio-Based Balance (approx.) |
|---|---|---|---|
| Soap Bar (super fatted talc bar) | 60-90% | Sodium $C_{14}$-$C_{24}$ fatty acid* soap | >95 wt % |
| | 10-40% | $C_{14}$-$C_{24}$ free fatty acids* | |
| | 0-10% | Glycerin* | |
| | 1-5% | Adjuvant: (e.g. talc, inorganic salts, fragrance, colorant, preservative, etc.) | |
| Liquid Body Wash or Shampoo | 3-15% | Sodium $C_{14}$-$C_{24}$ Alkyl* Ether Sulfate-3EO | >65 wt % |
| | 3-15% | $C_{14}$-$C_{24}$ Alkyl* Amidopropyl Betaine | |
| | 5-10% | $C_{14}$-$C_{24}$ Fatty Acid* Diethanolamide | |
| | 0.5-1% | Polyethylene Glycol-6000 di-$C_{14}$-$C_{24}$ *ester | |
| | q.s. | water | |
| Hard Surface Cleaner Concentrate | 10-15% | $C_{14}$-$C_{24}$ Fatty Alcohol* Ethoxylate-7EO | >50 wt % |
| | 5-10% | $C_{14}$-$C_{24}$ Fatty Acid* Diethanolamide | |
| | 20-25% | Sodium $C_{14}$-$C_{24}$ Alkyl* Ether Sulfate-3EO | |
| | 1-5% | Sodium Carbonate | |
| | 1-10% | Propylene* glycol diethyl* ether | |
| Spray and Wipe Hard Surface Cleaner (RTU) | 1-7% | Ethanol* | >65 wt % |
| | 1-7% | Propylene* glycol diethyl* ether | |
| | 1-5% | Ammonium $C_{14}$-$C_{24}$ Alkyl* Ether Sulfate-3EO | |
| | 1-2% | Ammonia | |
| | q.s. | Water | |
| Hand Dishwashing Liquid | 5-15% | α-Sulfonated $C_{14}$-$C_{24}$ Fatty Acid* Ethyl* Ester | >65 wt % |
| | 1-5% | $C_{14}$-$C_{24}$ Fatty Acid* Diethanolamide | |
| | 1-5% | Lecithin, 1,3-propane diol* or glycerin* | |
| | 5-15% | Sodium $C_{14}$-$C_{24}$ Alkyl* Ether Sulfate-3EO | |
| | q.s. | Water | |
| Laundry Detergent | 1-5% | α-Sulfonated $C_{14}$-$C_{24}$ Fatty Acid* Ethyl* Ester | >50 wt % |
| | 3-5% | $C_{14}$-$C_{24}$ Fatty Alcohol* Ethoxylate-7EO | |
| | 3-10% | Sodium $C_{14}$-$C_{24}$ Alkyl* Ether Sulfate-3EO | |
| | 1-5% | Sodium $C_{14}$-$C_{24}$ fatty acid* soap | |
| | 1-5% | Sodium Carbonate | |
| | q.s. | Water | | through simple organic reactions starting from algae bioorganic substances such as algae-triglycerides. This invention discloses many consumer products that may be formulated such that a majority of the carbon included within all of the ingredients is traceable back to algae origins.

We claim:

1. A bio-based non-food/non-fuel consumer product composition comprising at least one bio-derived ingredients collectively obtained as a mixture from algae through autotrophic or heterotrophic processes, wherein at least one ingredient includes a surfactant selected from the group of ethoxylated compounds consisting of fatty alcohol ethoxylates, ethoxylated fatty amines, ethoxylated fatty acid esters, and mixtures thereof, and wherein said ethoxylated compound(s) include ethylene oxide residues obtained from ethanol of algae origin.

2. The bio-based consumer product composition of claim 1 wherein the at least one ingredient further comprises at least one ingredient selected from the group consisting of emollients, skin benefit agents, structurants, rheology modifiers, and fillers, and mixtures thereof.

3. The bio-based consumer product composition of claim 2 further including an algae-derived solvent selected from the group consisting of ethanol, 1,3-propane diol, propylene glycol monoethyl ether and propylene glycol diethyl ether, and mixtures thereof.

4. The bio-based consumer product composition of claim 1, wherein said composition may be used for any one of skin cleansing, skin care, hair shampooing, hair care, fabric cleaning, fabric care, and hard surface cleaning.

5. The bio-based consumer product composition of claim 1, including at least two bio-derived ingredients collectively obtained as a mixture from algae through autotrophic or heterotrophic processes.

6. The bio-based consumer product composition of claim 1, wherein the at least one ingredient is obtained through synthetic organic reactions beginning from at least one algae-sourced biochemical.

7. The bio-based consumer product composition of claim 1, wherein the weight ratio among said ingredients in the said algae-derived mixture is controlled by selection of the alga/algae strain(s) and the growth conditions affecting the autotrophic or heterotrophic processes.

8. The bio-based consumer product composition of claim 1, wherein said algae-derived mixture have ingredient weight ratios ready for direct use in said compositions having use as skin cleansing, skin care, hair shampooing, hair care, laundry cleaning, fabric care, and household cleaning products.

9. The bio-based consumer production composition of claim 1, wherein said surfactant includes a carbon chain with at least eight contiguous carbons, said carbon chain directly traceable to algal origin.

10. The bio-based consumer production composition of claim 1, wherein said fatty acid soap is derived from $C_{14}$-$C_{24}$ algae fatty acid triglycerides through chemical or enzymatic lipidolysis.

11. The bio-based consumer production composition of claim 1, wherein said fatty acid soap is derived from $C_{14}$-$C_{24}$ algae fatty acid triglycerides through transesterifiction of the triglycerides with ethanol or methanol, distillation of the resulting fatty acid methyl or ethyl esters and hydrolysis of said esters to the free fatty soaps.

12. The bio-based consumer product composition of claim 1, wherein said at least one ingredient is algae-derived glycerin derived from chemical or enzymatic lipidolysis of algae fatty acid triglycerides.

13. The bio-based consumer product composition of claim 3, wherein said ethanol is obtained by enzymolysis and fermentation of algae-derived cellulose.

14. The bio-based consumer product composition of claim 1, wherein said ethanol is obtained through enzymolysis and fermentation of algal cellulose.

* * * * *